US010294180B2

(12) United States Patent
Van Der Waal et al.

(10) Patent No.: US 10,294,180 B2
(45) Date of Patent: May 21, 2019

(54) PROCESS FOR PREPARING ETHYLENE GLYCOL FROM A CARBOHYDRATE SOURCE

(71) Applicant: AVANTIUM KNOWLEDGE CENTRE B.V., Amsterdam (NL)

(72) Inventors: Jan Cornelis Van Der Waal, Amsterdam (NL); Gerardus Johannes Maria Gruter, Amsterdam (NL); Erik-Jan Ras, Amsterdam (NL)

(73) Assignee: AVANTIUM KNOWLEDGE CENTRE B.V., Amsterdam (NL)

( * ) Notice: Subject to any disclaimer, the term of this patent is extended or adjusted under 35 U.S.C. 154(b) by 0 days.

(21) Appl. No.: 15/543,091

(22) PCT Filed: Jan. 13, 2016

(86) PCT No.: PCT/NL2016/050027
§ 371 (c)(1),
(2) Date: Jul. 12, 2017

(87) PCT Pub. No.: WO2016/114659
PCT Pub. Date: Jul. 21, 2016

(65) Prior Publication Data
US 2017/0362145 A1    Dec. 21, 2017

(30) Foreign Application Priority Data

Jan. 13, 2015   (NL) ...................................... 2014118

(51) Int. Cl.
| | | |
|---|---|---|
| *B01J 23/46* | (2006.01) | |
| *B01J 23/62* | (2006.01) | |
| *B01J 23/89* | (2006.01) | |
| *B01J 37/02* | (2006.01) | |
| *B01J 37/18* | (2006.01) | |
| *C07C 29/60* | (2006.01) | |
| *C07C 29/82* | (2006.01) | |
| *C07C 31/20* | (2006.01) | |
| *C07C 29/132* | (2006.01) | |

(52) U.S. Cl.
CPC ........... *C07C 29/132* (2013.01); *B01J 23/462* (2013.01); *B01J 23/468* (2013.01); *B01J 23/626* (2013.01); *B01J 23/892* (2013.01); *B01J 23/8926* (2013.01); *B01J 37/0201* (2013.01); *B01J 37/0236* (2013.01); *B01J 37/18* (2013.01); *C07C 29/60* (2013.01); *C07C 29/82* (2013.01); *Y02P 20/52* (2015.11)

(58) Field of Classification Search
CPC ...... B01J 23/462; B01J 23/468; B01J 23/626; B01J 23/892; B01J 23/8926; B01J 37/0201; B01J 37/0236; B01J 37/18; C07C 29/132; C07C 29/60; C07C 29/82
See application file for complete search history.

(56) References Cited

U.S. PATENT DOCUMENTS

| | | | |
|---|---|---|---|
| 2,360,685 A | 10/1944 | Jensen | |
| 4,430,253 A | 2/1984 | Dubeck et al. | |
| 4,935,102 A | 6/1990 | Berg | |
| 4,966,658 A * | 10/1990 | Berg ...................... | C07C 29/82 203/62 |
| 5,423,955 A | 6/1995 | Berg | |
| 2008/0275277 A1 | 11/2008 | Kalagias | |
| 2011/0313209 A1 | 12/2011 | Kalnes et al. | |
| 2012/0172633 A1 | 7/2012 | Zhang et al. | |
| 2014/0288335 A1 | 9/2014 | Yoshii et al. | |
| 2015/0057469 A1 | 2/2015 | Zhang et al. | |
| 2015/0183701 A1 | 7/2015 | Blank et al. | |

FOREIGN PATENT DOCUMENTS

| | | | |
|---|---|---|---|
| CN | 101768050 A | | 7/2010 |
| CN | 102643164 | * | 8/2012 |
| CN | 102643165 A | | 8/2012 |
| CN | 102731253 A | | 10/2012 |
| CN | 102731253 B | | 10/2012 |
| CN | 102731255 A | | 10/2012 |
| CN | 102731256 B | | 10/2012 |
| CN | 103420797 A | | 12/2013 |
| CN | 103420797 B | | 12/2013 |
| CN | 104370692 B | | 2/2015 |

(Continued)

OTHER PUBLICATIONS

English translation of CN102643164, Aug. 22, 2012, pp. 1-9 (Year: 2012).*
International Search Report of Application No. PCT/NL2016/050027 dated Jun. 20, 2016.
Ji, N. et al., "Catalytic conversion of cellulose into ethylene glycol over supported carbide catalysts", Catalysis Today, Sep. 30, 2009, pp. 77-85, vol. 147, No. 2, Elsevier, NL.
Gang Xu et al., "Remarkable effect of extremely dilute H2SO4 on the cellulose conversion to ethylene glycol", Applied catalysis A: General, journal homepage: www.elseviercom/locate/apcata, 2015.
Yue Liu et al., "Kinetic insight into the effect of the catalytic functions on selective conversion of cellulose to polyols on carbon-supported WO3 and Ru catalysts", Catalysis Today, journal homepage: www.elsevier.com/locate/apcata, 2015.

(Continued)

*Primary Examiner* — Pancham Bakshi
*Assistant Examiner* — Mark R Luderer
(74) *Attorney, Agent, or Firm* — Thomas|Horstemeyer, LLP

(57) ABSTRACT

Ethylene glycol is prepared from a carbohydrate source in a process,
wherein hydrogen, the carbohydrate source, a liquid diluent and a catalyst system are introduced as reactants into a reaction zone;
wherein the catalyst system comprises a tungsten compound and ruthenium as hydrogenolysis metal and further at least one promoter metal, selected from transition and post-transition metals;
wherein the carbohydrate source is reacted with hydrogen in the presence of the catalyst system to yield a product mixture comprising ethylene glycol and butylene glycol. Butylene (Continued)

glycol may selectively be removed from the product mixture by azeotropic distillation using an entraining agent.

19 Claims, No Drawings

(56) References Cited

FOREIGN PATENT DOCUMENTS

| | | |
|---|---|---|
| CN | 104694671 | 6/2015 |
| EP | 0 343 475 A2 | 5/1989 |
| EP | 1 114 810 B1 | 7/2000 |
| WO | 20130015955 A2 | 1/2013 |
| WO | 20140173973 A1 | 10/2014 |
| WO | 2015/028398 A1 | 3/2015 |

* cited by examiner

PROCESS FOR PREPARING ETHYLENE GLYCOL FROM A CARBOHYDRATE SOURCE

CROSS-REFERENCE TO RELATED APPLICATION

This application is the National Stage of International Application No. PCT/NL2016/050027, filed 13 Jan. 2016, which claims the benefit of and priority to NL Application No. 2014118, having the title "Process For Preparing Ethylene Glycol From A Carbohydrate Source," filed on 13 Jan. 2015, the entire disclosures of which are incorporated by reference in their entireties as if fully set forth herein.

TECHNICAL FIELD

The present invention relates to a process for the preparation of ethylene glycol from a carbohydrate source. In particular it relates to a process for preparing ethylene glycol from a sustainable carbohydrate resource using a specific catalyst system.

BACKGROUND

The catalytic conversion of carbohydrates from a sustainable resource to valuable chemicals such as alkylene glycols has gained interest. Alkylene glycols are interesting chemicals that find application in the preparation of polyesters, such as poly(alkylene terephthalate), poly(alkylene naphthenate) or poly(alkylene furandicarboxylate). Further applications of alkylene glycols, in particular ethylene glycol, include its use as anti-freeze. By enabling the preparation of such chemicals from sustainable resources, the dependence of fossil fuel resources is reduced. Since there is a desire to reduce the dependence of fossil fuels there is a growing need for different sustainable resources for the production of alkylene glycols such as ethylene glycol.

In U.S. Pat. No. 7,960,594 a process is described wherein ethylene glycol is produced from cellulose. This process involves catalytic degradation and hydrogenation reactions under hydrothermal conditions. More in particular, the process is carried out by contacting cellulose at elevated temperature and pressure with a catalyst system comprising two sorts of active components in the presence of hydrogen. The first active component comprises tungsten or molybdenum in its metallic state or its carbide, nitride or phosphide. The second component is selected from the hydrogenation metals from Groups 8, 9 and 10 of the Periodic Table of Elements, and includes cobalt, nickel, ruthenium, rhodium, palladium, iridium and platinum. In experiments the compounds were used on a carrier, such as activated carbon. Moreover, it appears that the reaction conditions that results in satisfactory yields include a temperature of 220-250° C. and a hydrogen pressure of 3 to 7 MPa (measured at room temperature). When a 1% wt slurry of cellulose is subjected to these compounds for 30 minutes, ethylene glycol is obtained in yields of up to 69%. However, it also appears that when the reaction is continued for a prolonged period the ethylene glycol yield reduces.

In U.S. Pat. No. 8,410,319 a continuous process is described wherein a cellulose-containing feedstock is contacted with water, hydrogen and a catalyst to generate at least one alkylene glycol. The catalyst comprises a first metal component selected from the group consisting of Mo, W, V, Ni, Co, Fe, Ta, Nb, Ti, Cr, Zr and combinations thereof. The first metal component is in the elemental state or the metal is the carbide, nitride or phosphide compound. The catalyst further comprises Pt, Pd, Ru and combinations thereof, wherein the metal is in the elemental state. The catalyst components are comprised on a carrier.

This reaction has been further studied on catalyst systems that contain nickel and tungsten on a carrier. There it has been found that nickel and tungsten are leached into the solution during the reaction, which accounts for the gradual deterioration of the catalyst performance (cf. Na Ji et al., ChemSusChem, 2012, 5, 939-944). The leaching of tungsten and other metals has been confirmed in the study reported in M. Zheng et al., Chin. J. Catal., 35 (2014) 602-613. The latter document also discloses that in addition to ethylene glycol different by-products are obtained, including 1,2-propylene glycol, erythritol, glycerol, mannitol and sorbitol.

US 2011/0312488 describes a catalyst system for the generation of alkylene glycols from a carbohydrate as a potential alternative for a catalyst containing the metal components in the elemental state; this catalyst system comprises at least one metal with an oxidation state of at least +2. More in particular this US application discloses a catalyst system comprising a first metal component with an oxidation state of at least +2 and a hydrogenation component. The hydrogenation component can be selected from a wide range of metals in any oxidation state, including in the elemental state. The hydrogenation component may in particular comprise an active metal component selected from the group consisting of Pt, Pd, Ru, Rh, Ni, Ir and combinations thereof. The first metal component may also be selected from a range of metals, but in particular the compounds comprising the first metal component may be selected from the group comprising tungstic acid, molybdic acid, ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxides, heteropoly compounds of tungsten and various salts and oxides of molybdenum, niobium, vanadium, zirconium, titanium and chromium. The catalyst system according to US 2011/0312488 is stated to improve the selectivity to ethylene glycol and propylene glycol, with a reduced production of butane diols. The ethylene glycol generation is shown in some experiments, indicating that ammonium metatungstate is the preferred first metal component and that as preferred hydrogenation component platinum and nickel may be used. The use of nickel-containing catalyst systems results in the highest yields of ethylene glycol and optionally propylene glycol.

In the above-mentioned article of M. Zheng et al., Chin. J. Catal., 35 (2014) 602-613, the conclusion is drawn that tungsten acid-based catalysts are the most promising candidates for future commercialization of the cellulose-to-ethylene-glycol process. A hydrogenation component is added to such tungsten acid-based catalysts. Examples include ruthenium on activated carbon, but Raney nickel is considered the most promising candidate for commercialization.

The conversion of a carbohydrate to alkylene glycol involves complex reactions. It has been shown in M. Zheng et al., Chin. J. Catal., 35 (2014) 602-613, that lower concentrations of carbohydrate and high reaction temperatures, i.e. above 200° C., are beneficial to ethylene glycol production. This appears to be confirmed in WO 2014/161852, containing experiments wherein glucose solutions with increasing glucose concentrations, ranging from 1% wt to 6% wt, were contacted with hydrogen in the presence of a catalyst system comprising tungsten and ruthenium. The higher the glucose concentration was, the lower the yield of ethylene glycol became. In order to remedy this disadvantageous effect, it is proposed in WO 2014/161852 to contact a first small portion of the carbohydrate with hydrogen and the catalyst in a solution with a carbohydrate concentration of less than 2% wt, and only when the first portion has reacted, to add further portions of the carbohydrate. In this respect the process is similar to the semi-continuous reactions described in G. Zhao et al., Ind. Eng. Chem. Res., 2013, 52, 9566-9572. Both WO 2014/161852 and G. Zhao et al. in Ind. Eng. Chem. Res., 2013, 52, 9566-9572, mention that, in addition to ethylene glycol, 1,2-butane diol (butylene glycol) is produced. The relative amount of butylene glycol can be in the order of 10%, based on the yield of ethylene glycol. Since butylene glycol and ethylene glycol form an azeotrope, it is difficult to separate the compounds easily via distillation.

SUMMARY

Therefore there is a desire to increase the yield of ethylene glycol and reduce the relative amount of butylene glycol. There is further a need for an easy separation method for removing this relatively small amount of butylene glycol. It has been found that the use of a ruthenium-containing catalyst system that further comprises at least one other promoter metal increases the yield of ethylene glycol.

Accordingly, the present invention provides a process for preparing ethylene glycol from a carbohydrate source, wherein hydrogen, the carbohydrate source, a liquid diluent and a catalyst system are introduced as reactants into a reaction zone;

wherein the catalyst system comprises a tungsten compound and ruthenium as hydrogenolysis metal and further at least one promoter metal, selected from transition and post-transition metals;

wherein the carbohydrate source is reacted with hydrogen in the presence of the catalyst system to yield a product mixture comprising ethylene glycol and butylene glycol.

DETAILED DESCRIPTION

The process according to the present invention employs a catalyst system that, in addition to a tungsten compound, comprises ruthenium and at least one other transition or a post-transition metal. By post transition metals are understood those elements classified as post-transition metals by W. Masterton, C. Hurley & E. Neth, 2011, Chemistry: Principles and Reactions, 7th ed., Brooks/Cole, Belmont, Calif., ISBN 1-111-42710-0, viz., Ga, In, Tl, Sn, Pb, Bi and Po. It has been found that out of the post-transition metals, tin is very suitable. The transition metals comprise the elements in groups 3 to 12. Out of the transition metals, not only the other hydrogenolysis metals from the groups 8, 9 and 10 of the Periodic Table of Elements can be selected, but also the metals from groups 11 and 12 have been found to be very suitable. The at least one other transition metal is preferably selected from Cu and the other hydrogenolysis metals from groups 8, 9 and 10 of the Periodic Table of Elements. Hydrogenolysis metals may suitably be selected from the group consisting of Fe, Ni, Co, Pt, Pd, Rh, Ir, and combinations thereof. Preferably, the hydrogenolysis metal is selected from the noble metals Pd, Pt, Ru, Rh, Ir and combinations thereof. It has been found that these metals give good yields. The metal may suitably be present in its metallic form or as its hydride or oxide. It is assumed that the metal oxide will be reduced during the reaction in the presence of hydrogen.

The preferred metal combinations are those comprising ruthenium with one or more of the metals selected from Cu, Ni, Sn, Pt, Pd, Ir and Rh, Ruthenium and the at least one promoter metal are preferably present in the form of a catalyst supported on a carrier. The carrier may be selected from a wide range of known supports. Suitable supports include activated carbon, silica, zirconia, alumina, silica-alumina, titania, niobia, iron oxide, tin oxide, zinc oxide, silica-zirconia, zeolitic aluminosilicates, titanosilicates, magnesia, silicon carbide, clays and combinations thereof. The skilled person will know that activated carbon is an amorphous form of carbon with a surface area of at least 800 $m^2/g$. Such activated carbon thus has a porous structure. Most preferred supports are activated carbon, silica, silica-alumina and alumina, since excellent results have been obtained therewith. More preferably, the catalyst comprises activated carbon as the support.

The metals, i.e. ruthenium and the promoter metal or metals, are suitably included on the carrier by impregnation. The impregnation can be achieved by impregnation of an aqueous solution of a metal salt with subsequent removal of water. Calcination may result in the metal oxide, which can subsequently be reduced to yield the metal in its metallic form. It has been surprisingly found that the best results are obtainable when ruthenium and the at least one promoter metal are co-impregnated. When catalysts are used that have similar or the same compositions, but that differ in their preparation methods, it appears that the catalyst that has been prepared by co-impregnation performs better than similar catalysts that have been prepared by subsequent impregnations. Without wishing to be bound by any theory it is believed that the metals during co-impregnation are intimately mixed and by the calcinations and subsequent reduction form an alloy that provides the better performance.

The amount of the promoter metal or promoter metals is suitably selected such that the amount of promoter metal or metals is at most equal 50% wt, based on the weight of ruthenium. The weight ratio of ruthenium to promoter metal or metals is suitably in the range of 2:1 to 100:1. More preferably, the weight ratio between Ru and the promoter metal or promoter metals is in the range of 10:1 to 70:1.

In the process of the present invention any butylene glycol formed may suitably be selectively removed from the product mixture by azeotropic distillation using an entraining agent.

The entraining agent selectively removes butylene glycol from a mixture of alkylene glycols by means of azeotropic distillation. The entraining agent can suitably be selected from the group of hydrocarbon compounds, preferably consisting of ethyl benzene, p-xylene, n-propyl benzene, o-diethyl benzene, m-diethyl benzene, m-di-isopropyl benzene, cyclopentane, methyl cyclohexane, 3-methyl pentane, 2,3-dimethyl butane, heptane, 1-heptene, octane, 1-octene, 2,3,4-trimethyl pentane, decane, decalin, dicyclo pentadiene, alpha-phellandrene, beta-pinene, myrcene, terpinolene, p-mentha-1,5-diene, 3-carene, limonene and alpha-terpinene. A suitable heteroatom-containing compound is methyl ethyl ketoxime, In addition, higher polyols, such as glycerol, erythritol, or sorbitol may function as an entraining agent. These compounds tend to be produced as by-products in the process for preparing ethylene glycol from carbohydrates, as shown in M. Zheng et al., Chin. J. Catal., 35 (2014) 602-613. These compounds may therefore be recycled to the process after separation from the butylene glycol. If necessary, one or more of these compounds can also be added to the product of the present process in order to enhance their concentrations and facilitate thereby the obtaining of pure ethylene glycol, when they are used as entraining agents.

The procedure for performing an azeotropic or extractive distillation using entraining agents is known for the skilled person. Typically the product mixture is mixed with the entraining agent and the resulting admixture is subjected to azeotropic distillation. Generally, the entraining agent is selected such that the azeotrope of the butylene glycol and entraining agent has a boiling point below the boiling point of ethylene glycol. More preferably, the entraining agent is not soluble or miscible with butylene glycol, so that after distillation the condensate will form two liquid phases, thereby facilitating the recovery of the entraining agent. The recovered entraining agent may suitably be recycled to the azeotropic distillation. Butylene glycol may optionally be further purified, and used for several applications.

Such further purification may e.g. entail that crude butylene glycol is converted to dioxolane using a carbonyl group-containing compound. The resulting dioxolane-containing mixture is then subjected distillation. The various dioxolane compounds derived from different alkylene glycols can be easily separated by distillation. Other mono- or polyalcohols that may be present are also easily separated in this way. Hence a pure dioxolane, derived from butylene glycol is obtained. The dioxolane can subsequently be converted into butylene glycol and carbonyl group-containing compound.

The distillation conditions for mixtures of alkylene glycols are known in the art. These conditions tend to include temperatures up to 200° C. and pressures that may vary from vacuum, e.g. 50 mbar, to atmospheric.

The carbohydrate source can be selected from a variety of sources. Suitably, the carbohydrate source contains or consists of a carbohydrate selected from the group consisting of polysaccharides, oligosaccharides, disaccharides, and monosaccharides. Suitable examples include sustainable sources such as cellulose, hemicellulose, hemicelluloses sugars, starch, sugars, such as sucrose, mannose, arabinose, glucose and mixtures thereof. Sources that may include the above carbohydrates include paper pulp streams, municipal waste water streams and other glucose units-containing streams can be used as well, for example from wood waste, paper waste, agricultural waste, municipal waste, paper, cardboard, sugar cane, sugar beet, wheat, rye, barley, other agricultural crops and combinations thereof. These streams may require pre-treatment to remove components that interfere with the present process such as basic fillers, e.g. calcium carbonate in waste paper. In this way the process according to the invention may not only be used from natural sources, but can even be used to upgrade and usefully re-use waste streams. Preferably, the carbohydrate in the carbohydrate source is selected from the group consisting of cellulose, starch, glucose, sucrose, glucose-oligomers, paper waste, and combinations thereof, preferably glucose or starch. Since cellulose presents difficulties that are absent in other carbohydrate sources, the carbohydrate source is preferably selected from the group consisting of starch, hemicellulose and hemicellulose sugars, glucose and combinations thereof.

The tungsten compound can be selected from a wide range of compounds. The tungsten may be in the elemental state. Usually, the tungsten compound is then present on a support. Similar to the supports for the at least one hydrogenolysis metal, the support may be selected from a wide range of known supports. Suitable supports include active carbon, silica, zirconia, alumina, silica-alumina, titania, niobia, iron oxide, tin oxide, zinc oxide, silica-zirconia, zeolitic aluminosilicates, titanosilicates and combinations thereof. Most preferred are activated carbon, silica, silica-alumina and alumina as support, since excellent results have been obtained therewith. It is also possible to use tungsten compounds in an oxidation state of up to +2, such as in the form of its carbide, nitride or phosphide. Also in this case the tungsten compound may be present in the form of a supported catalyst component. The carrier may be selected from the supports described hereinabove.

Preferably, the tungsten compound has an oxidation state of at least +2, preferably having an oxidation state of +5 or +6. The tungsten compound is then suitably selected from the group consisting of tungstic acid ($H_2WO_4$), ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxide ($WO_3$), heteropoly compounds of tungsten, and combinations thereof. Whereas in the prior art it has been found that certain tungsten compounds leached from their supports and that such was considered a disadvantage, the present inventors have found that it is advantageous to use tungsten compounds that dissolve in the reaction mixture. It has been found that the catalytic activity of the tungsten compound increases if the tungsten compound is dissolved. Without wishing to be bound to any theory it is believed that in the reducing atmosphere that is created in the reaction zone by means of the presence of hydrogen, hexavalent tungsten compounds may be reduced to pentavalent tungsten and the pentavalent tungsten compound may dissolve into the diluent. In this partly reduced state the tungsten ions are effective in attacking the carbon bonds in the carbohydrate source and form alkylene glycol precursors. Therefore, a preferred tungsten compound is tungstic acid. In this context it is noted that it has been found that polyols, including alkylene glycols, facilitate the dissolution of the tungsten compound into the diluent, thereby promoting the catalytic activity of the tungsten compound. The use of alkylene glycol as diluent is particularly suitable as such use does not involve the introduction of an extraneous reagent into the reaction mixture, which represents a further advantage.

According to the prior art the ratio between the hydrogenolysis metal and the tungsten compound may vary between wide ranges. According to the prior art the weight ratio between these components may vary from 0.02 to 3000. In the present invention the molar ratio of tungsten to ruthenium is preferably in the rather narrow range of 1 to 25. More preferably the molar ratio of tungsten to ruthenium is in the range of 2 to 20, most preferably from 10 to 20. If the ratio is beyond the limits of these ranges, the relative yield of alkylene glycols other than ethylene glycol is decreased and/or the conversion of the carbohydrate is slowed down.

The concentrations of the catalyst components may vary in the process according to the present invention. The concentration of the tungsten compound may vary between very wide ranges. The concentration of the tungsten compound may for instance be selected from the range of 1 to 35% wt, calculated as tungsten and based on the weight of the carbohydrate source introduced into the reaction zone. More preferably, the amount of tungsten is in the range of 2 to 25% wt, based on the carbohydrate source introduced into the reaction zone. Since the use of relatively high amounts of tungsten does not add significant advantages to the process whereas the costs aspect may become significant, it is preferred to use amounts of tungsten of 5 to 20% wt, based on the amount of carbohydrate source.

The amount of ruthenium as hydrogenolysis metal and the promoter metal or metals preferably ranges from 0.2 to 1.0% wt, calculated as metals and based on the amount of carbohydrate source introduced into the reaction zone. The weight ratio between ruthenium and the promoter metal or metals is suitably in the range as indicated above, i.e. in the range of 2:1 to 100:1.

The carbohydrate source and the diluent are both introduced into the reaction zone. Suitably, the carbohydrate source is introduced together with at least part of the diluent. More preferably, the carbohydrate source is at least partially dissolved in the diluent. Suitably, the diluent is an aqueous medium. In the process of the present invention the diluent comprises suitably at least water and an alkylene glycol. Many carbohydrates such as sugars, glucose and fructose are soluble in water. Moreover, cellulose, i.e. a carbohydrate that is regarded as a very suitable starting material, and that is insoluble in water, can be converted into cellodextrins which are water-soluble. Alternatively, the carbohydrate may be introduced into the reaction zone in the form of a slurry. The more common examples of such slurries are aqueous mixtures of water and cellulose and/or starch. In such embodiments aqueous cellulose slurries, containing e.g. microcrystalline cellulose, can suitably be used.

The concentration of the carbohydrate source in the diluent can vary. For a commercially interesting operation higher concentrations are desirable. However, the skilled person is taught that at increasing concentration the yield of alkylene glycols will decrease.

Typically three modes of operation are feasible. The first mode is a batch operation in which the carbohydrate source, the diluent and the catalyst system are introduced into a reaction zone, exposed to hydrogen and reacted. In such a situation, the concentration of the carbohydrate source in the diluent is suitably from 1 to 25% wt.

A second mode is a method similar to the method according to WO 2014/161852, wherein a reaction zone is charged with the catalyst system, a diluent and a small amount of carbohydrate source, and wherein the amount of carbohydrate source is reacted with hydrogen whilst additional carbohydrate source is added with or without additional diluent. The reaction is then led to completion. The eventual amount of carbohydrate source added to the reaction zone is then suitably in the range of 10 to 35% wt, calculated as carbohydrate source based on the amount of diluent.

The third mode of operation is a continuous operation. In one continuous operation mode a feedstock comprising at least the diluent and the carbohydrate source is passed through a plug flow reactor in the presence of hydrogen and also in the presence of a catalyst system. The concentration of the carbohydrate in the diluent may suitably be in the range of 1 to 15% wt of carbohydrate source, calculated as amount of carbohydrate source per amount of diluent. Other continuous reactors include slurry reactors and ebullating bed reactors.

A preferred embodiment of a continuous mode is to use a continuous stirred tank reactor (CSTR). The use of a CSTR is very suitable for the present process as the diluent in the CSTR provides an excellent means for diluting the eventual concentration of the carbohydrate in the CSTR, whereas the feed stream may comprise a high concentration of carbohydrate. The feed stream to the CSTR may comprise pure carbohydrate. Preferably, the feed stream is a solution or slurry of the carbohydrate in the diluent. The carbohydrate concentration in the feed stream can be rather high, since the CSTR contains a reaction medium that comprises the catalyst system, a mixture of product and carbohydrate source and diluent. During operation the CSTR is fed with one or more feed streams comprising carbohydrate source, diluent and optionally some or all of the components of the catalyst system, and from the CSTR a product stream comprising the alkylene glycol-containing product mixture, diluent and optionally some or all of the components of the catalyst system is removed. In addition to the diluent and the carbohydrate source, also additional tungsten compound can be fed continuously or periodically to make up for any tungsten that is dissolved in the reaction mixture during the reaction, and subsequently removed from the reactor. The carbohydrate concentration in the feed stream may be rather high, and be in the range of 10 to 50% wt, calculated as amount of carbohydrate source per amount of diluent. The alkylene glycols that are produced by the reaction of the carbohydrate source provide a medium wherein tungsten compounds may be dissolved, thereby benefitting the catalytic activity of the tungsten catalyst component. The present invention therefore also provides for an embodiment wherein the present process is conducted in a CSTR wherein hydrogen, the carbohydrate source and the liquid diluent are continuously fed to the CSTR, and wherein continuously a product mixture comprising alkylene glycol and diluent is removed from the CSTR.

The process of the present invention allows for embodiments wherein high concentrations of carbohydrate source in the diluent, e.g. from 4 to 50% wt, are envisaged. The high concentration may pose problems vis-à-vis the solubility of the carbohydrate source. The diluent may comprise an alkylene glycol. The alkylene glycol suitably has 2 to 6 carbon atoms. Suitable alkylene glycols include 1,6-hexane diol, butylene glycol and propylene glycol. When butylene glycol is added as extra component to the diluent this butylene diol needs to be removed from the eventual product mixture. That may require an undesirably high energy input. Thus, the most preferred alkylene glycol is ethylene glycol. The diluent further typically includes water as diluent. It also functions as solvent for most of the carbohydrate sources. The amount of alkylene glycol in the diluent is suitably in the range of 2 to 25% vol, based on the volume of water and alkylene glycol. The preferred diluent is therefore a mixture of alkylene glycol, in particular ethylene glycol, and water, wherein the amount of alkylene glycol ranges from 2 to 25% vol, based on the volume of water and alkylene glycol.

In addition, the skilled person may desire to add other compounds to the diluent. Such other diluents may be selected from the group consisting of sulfoxides, alcohols other than alkylene glycols, amides and mixtures thereof. A suitable sulfoxide is dimethyl sulfoxide (DMSO); suitable examples of amides are dimethyl formamide and dimethyl acetamide. The more preferred organic diluents are the alcohols. The alcohols can be mono-alcohols, in particular water-miscible mono-alcohols, such as $C_1$-$C_4$ alcohols. The alcohol may also be a polyol, e.g. glycerol, sorbitol, xylytol or erythritol.

The prior art processes focus on the conversion of hexoses, such as cellulose, starch and glucose. However, it has been found that it is advantageous to use not only hexose-containing carbohydrates, but also pentose-containing carbohydrates. Therefore the present invention also provides a process wherein the carbohydrate source comprises at least one pentose-containing carbohydrate or, preferably, the carbohydrate source comprises a combination of at least one pentose-containing carbohydrate and at least one hexose-containing carbohydrate. The pentose-containing carbohydrate may be a polysaccharide, an oligosaccharide, a disaccharide or a monosaccharide. The pentose-containing carbohydrate is suitably a pentosan, for instance xylan or arabinan. In particular, it comprises suitably at least one of arabinose, ribose, lyxose and xylose moieties. The application of the process according to the present invention on a combination of hexose- and pentose-containing carbohydrates has the advantage that the pentose-containing carbohydrate yields both propylene glycol and ethylene glycol as main products, and the hexose-containing carbohydrates yield a majority of ethylene glycol. Hence, when propylene glycol is envisaged as a main by-product, the use of pentose-containing carbohydrate as starting material is beneficial. It is evident that the carbohydrate source that comprises hexose and pentose units may be obtained by mixing a separate hexose and a separate pentose fraction. Alternatively, the carbohydrate source may be the product of a natural source that already contains pentose and hexose units. It may e.g. be the hydrolysis product of lignocellulosic biomass, which hydrolysis results in both pentoses and hexoses.

As indicated above, the ethylene glycol-containing product of the process according to the present invention generally is a mixture of alkylene glycols. This mixture is suitably purified, especially when pure ethylene glycol is desired for polymerization purposes. The azeotrope that is formed with butylene glycol makes it difficult to obtain pure ethylene glycol. Therefore, an entraining agent is used in accordance with the present invention.

To facilitate the separation process it is advantageous to use also pentose-containing carbohydrate as starting material. Pentose-containing carbohydrates form hardly any butylene glycol as by-product. Hence, the proportion of butylene glycol in the reaction product of a combination of pentose- and hexose-containing carbohydrates will be relatively small. The purification of such a reaction product in accordance with the invention is therefore relatively simple. Propylene glycol and ethylene glycol can be easily separated from each other by means of fractionation. Fractionation of the product of the reaction with a starting material that comprises both pentose- and hexose-containing carbohydrates will result in pure ethylene glycol, pure propylene glycol and a relatively small fraction containing butylene glycol with one or both of the other glycols, which may then be treated with an entraining agent.

The process for the preparation of ethylene glycol according to the present invention can be carried out under the process conditions that are known in the art. The conditions include those that are disclosed in WO 2014/161852. Hence, the reaction temperature is suitably at least 120° C., preferably at least 140° C., more preferably at least 150° C., most preferably at least 160° C. The temperature in the reactor is suitably at most 300° C., preferably at most 280° C., more preferably at most 270° C., even more preferably at most 250° C., and most preferably at most 200° C. The reactor may be brought to a temperature within these ranges before addition of any starting material and is maintained at a temperature within the range.

It has been found that the process according to the present invention more advantageously is carried out at temperatures that are generally somewhat lower than those used in the prior art processes. It has been found that the formation of butylene glycol is reduced if relatively low temperatures are employed. The more advantageous temperature range is from 150 to 225° C., more preferably from 160 to 200° C., and most preferably from 165 to 190° C. This is contrary to what is taught in U.S. Pat. No. 7,960,594 wherein a reaction temperature in the range 220-250° C. was stated to be most useful.

The process of the present invention takes place in the presence of hydrogen. The hydrogen can be supplied as substantially pure hydrogen. The total pressure will then be the hydrogen pressure. Alternatively, the hydrogen may be supplied in the form of a mixture of hydrogen and an inert gas. The total pressure will then consist of the partial pressures of hydrogen and this inert gas. The inert gas can suitably be selected from nitrogen, argon, neon, helium and mixtures thereof. The ratio of hydrogen to the inert gas may vary between wide ranges. Suitably, the ratio is not very low, since the reaction proceeds well when the hydrogen partial pressure is sufficiently high. Accordingly, the volume ratio between hydrogen and the inert gas may be from 1:1 to 1:0.01. More preferably, only hydrogen is used as gas in the process according to the invention.

The pressure in the reactor is suitably at least 1 MPa, preferably at least 2 MPa, more preferably at least 3 MPa. The pressure in the reactor is suitably at most 16 MPa, more preferably at most 12 MPa, more preferably at most 10 MPa. Preferably, the reactor is pressurized by addition of hydrogen before addition of any starting material. The skilled person will understand that the pressure at 20° C. will be lower than the actual pressure at the reaction temperature. The pressure applied in the process is suitably 0.7 to 8 MPa, determined at 20° C. The pressure may be applied by hydrogen gas or a hydrogen-containing gas. When a hydrogen-containing gas is used, the hydrogen content in the hydrogen-containing gas may be up to 100 vol %, e.g. in the range of 5 to 95 vol %. The balance of the hydrogen-containing gas may suitably be an inert gas, such as nitrogen, helium, neon, argon or mixtures thereof, as indicated hereinbefore. When the reaction mixture is subsequently heated the pressure at reaction is suitably in the range of 1 to 16 MPa. As the reaction proceeds some hydrogen is consumed. Advantageously, the hydrogen partial pressure at reaction temperature is maintained within the range of 1 to 16 MPa. It is further preferred to maintain the hydrogen pressure or hydrogen partial pressure within the range during the entire reaction. Therefore hydrogen or hydrogen-containing gas may be introduced into the reaction mixture during the reaction.

The process of the present invention may suitably be used as the first step in starting a continuous process. In such a process the reaction is started with a mixture of carbohydrate, diluent, catalyst system and hydrogen, wherein the diluent comprises an alkylene glycol. When the reaction mixture has started to react and the carbohydrate conversion has resulted in the formation of ethylene glycol, a continuous stream of carbohydrate, diluent and optionally catalyst components may be fed to the reaction zone and a continuous stream of alkylene glycol-containing product mixture may be withdrawn from the reaction zone.

Although in a batch or semi-continuous process there may not be a need for it, it is possible to add extra catalyst components such as tungsten compound or the hydrogenolysis metal to the reaction mixture during the course of the reaction. Such may be found desirable when the reaction is prolonged and the concentration of the catalyst system gets below a desired level, due to the addition of diluent and/or carbohydrate.

The reaction zone is typically located in a reactor. The reactor in the present invention may be any suitable reactor known in the art. For a batch process and for the semi-continuous process the reactor can be a typical batch reactor.

That means that it comprises a pressure vessel, provided with the appropriate number of inlets for the introduction of the starting material, diluent and catalyst system, as well as an inlet for hydrogen-containing gas. The vessel is typically provided with a stirring or agitation means. For a continuous process the reactor may be selected from a variety of reactors, including a trickle flow reactor, a fluidized bed reactor, a slurry reactor, an ebullating bed reactor, a plug flow reactor and a continuous stirred tank reactor (CSTR). The use of a CSTR is very suitable for the present process as indicated above.

The reaction time in the process according to the present invention may vary. Suitably the residence time of the carbohydrate source is at least 1 min. Preferably the residence time is in the range of 5 min to 6 hrs, more preferably from 5 min to 2 hr. In a batch process the residence time is the time during which the carbohydrate source is contacted with hydrogen and the catalyst system under reaction conditions. In a continuous process the residence time is understood to be the quotient of the mass flow rate of the carbohydrate source into the reaction zone divided by the mass flow rate of the catalyst system in the reaction zone. In general a continuous process is operated at a weight hourly space velocity (WHSV), expressed as the mass of carbohydrate source per mass of hydrogenolysis metal, expressed as metal, per hour, in the range of 0.01 to 100 $hr^{-1}$, preferably from 0.05 to 10 $hr^{-1}$.

The invention is further illustrated by means of the following Examples.

EXAMPLES

General Procedure

The experiments were conducted according to the following procedure. An amount of 100 mg of feedstock and 1000 µl of water were added to an 8 ml autoclave reactor. An amount of hydrogenolysis catalyst and $H_2WO_4$ as tungsten compound was added to the reactor. Details of the feedstocks and type and amounts of catalysts are shown in the Tables. The autoclave was sealed and purged with $N_2$ followed by $H_2$ and finally pressurized to 50 bar with $H_2$ at room temperature. The autoclave was heated up to 190° C., with constant stirring at about 900 rpm and kept at temperature for 90 minutes. After 90 minutes, the autoclave was cooled down to room temperature and liquid product was analyzed using gas chromatography.

Hydrogenolysis catalysts were prepared by co-impregnation of activated carbon with a solution of ruthenium nitrate and a salt of another metal (Cu, Ni, Pd, Pt or Sn nitrate, or Ir acetate) in water. The impregnated support was then dried at room temperature overnight and at 80° C. for five hours. Subsequently, the dried catalyst thus obtained was reduced in a flow of $H_2$-containing gas at 250° C. for 2 hours.

Example 1

Hydrogenolysis catalysts having the composition as indicated in Table 1 were used, together with tungstic acid, in the conversion of glucose with hydrogen using the general procedure as described above. The catalysts contained 0.1 or 0.5% wt of promoter metal and 4.9 or 4.5% wt of ruthenium, respectively, calculated as metal on the hydrogenolysis catalyst. The total amount of metal was 5% wt for each catalyst. The amounts of hydrogenolysis catalysts, calculated as milligram metals per liter water, were 10 mg/l; the amount of tungstic acid in each experiment was 10 mg/l water. The results are shown in Table 1.

The table shows the yields of ethylene glycol (yEG), propylene glycol (yPG) and butylene glycol (yBG), calculated as the percentage of grams obtained divided by the amount of grams glucose as starting material.

TABLE 1

| Exp. No. | Catalyst No. | Promoter metal | Amount, % wt | Ru, Amount, % wt | yEG, % | yPG, % | yBG, % |
| --- | --- | --- | --- | --- | --- | --- | --- |
| 1 | Cat. 1 | — | — | 5 | 12.6 | 1.5 | 0.9 |
| 2 | Cat. 2 | Ni | 0.1 | 4.9 | 19.3 | 2.0 | 1.5 |
| 3 | Cat. 3 | Cu | 0.1 | 4.9 | 22.0 | 2.6 | 2.0 |
| 4 | Cat. 4 | Pd | 0.1 | 4.9 | 22.3 | 3.2 | 2.9 |
| 5 | Cat. 5 | Pt | 0.1 | 4.9 | 21.6 | 2.7 | 1.3 |
| 6 | Cat. 6 | Pt | 0.5 | 4.5 | 20.6 | 2.3 | 1.7 |
| 7 | Cat. 7 | Ir | 0.1 | 4.9 | 14.7 | 1.6 | 0.8 |
| 8 | Cat. 8 | Sn | 0.1 | 4.9 | 22.2 | 2.8 | 2.5 |

Experiment No. 1 is a comparative experiment. The results show that the use of a promoter metal increases the yield of ethylene glycol. Comparison between the results of experiment Nos. 5 and 6 shows that the increase of promoter metal not necessarily increases the yield.

Example 2

A series experiments were conducted in the same manner as for the experiments of Example 1, the only difference being that the amounts of hydrogenolysis catalysts, calculated as milligram metals per liter water, and the amounts of tungstic acid were halved to 5 mg/ml.

The results are shown in Table 2.

TABLE 2

| Exp. No. | Catalyst No. | Promoter metal | Amount, % wt | Ru, Amount, % wt | yEG, % | yPG, % | yBG, % |
| --- | --- | --- | --- | --- | --- | --- | --- |
| 9 | Cat. 1 | — | — | 5 | 24.1 | 3.4 | 3.9 |
| 10 | Cat. 2 | Ni | 0.1 | 4.9 | 19.8 | 2.2 | 5.0 |
| 11 | Cat. 3 | Cu | 0.1 | 4.9 | 24.3 | 3.5 | 4.0 |
| 12 | Cat. 4 | Pd | 0.1 | 4.9 | 25.0 | 2.2 | 4.4 |
| 13 | Cat. 5 | Pt | 0.1 | 4.9 | 24.2 | 3.6 | 4.1 |
| 14 | Cat. 6 | Pt | 0.5 | 4.5 | 20.7 | 4.3 | 5.3 |
| 15 | Cat. 7 | Ir | 0.1 | 4.9 | 23.0 | 4.0 | 4.7 |
| 16 | Cat. 8 | Sn | 0.1 | 4.9 | 21.7 | 4.2 | 5.1 |

The results show that surprisingly the yield of butylene glycol increases when a smaller amount of catalyst is used in the reaction. In many instances, the yield of ethylene glycol also increases.

Example 3

To show the suitability of the catalysts systems for the conversion of carbohydrates, other than glucose, a series of experiments was conducted with starch as feedstock, in the same starting concentration as that of glucose in the other experiments, i.e. 100 mg/l. The reactions were conducted in accordance with the General Procedure as described above. The amounts of hydrogenolysis catalysts were in all experiments 5 mg metals/ml water. The amount of tungstic acid was in each experiment 10 mg/ml.

The catalysts and the results are shown in Table 3.

TABLE 3

| Exp. No. | Catalyst No. | Promoter metal | Amount, % wt | Ru, Amount, % wt | yEG, % | yPG, % | yBG, % |
|---|---|---|---|---|---|---|---|
| 17 | Cat. 1 | — | — | 5.0 | 14.4 | 3.4 | 6.3 |
| 18 | Cat. 2 | Ni | 0.1 | 4.9 | 22.3 | 4.1 | 6.8 |
| 19 | Cat. 3 | Cu | 0.1 | 4.9 | 15.0 | 4.1 | 6.9 |
| 20 | Cat. 4 | Pd | 0.1 | 4.9 | 15.1 | 4.0 | 6.7 |
| 21 | Cat. 5 | Pt | 0.1 | 4.9 | 17.2 | 4.4 | 7.2 |
| 22 | Cat. 7 | Ir | 0.1 | 4.9 | 17.8 | 4.2 | 7.1 |
| 23 | Cat. 8 | Sn | 0.1 | 4.9 | 20.4 | 4.7 | 6.9 |
| 24 | Cat. 9 | Sn | 0.5 | 4.5 | 9.9 | 1.3 | 1.6 |
| 25 | Cat. 10 | Sn | 1.0 | 4.0 | 11.0 | 1.2 | 1.3 |

The results show that the use of a promoter metal in the catalyst system entails an increased amount of ethylene glycol and butylene glycol. Comparison of the results of experiments Nos. 23 to 25 confirms that the increase of the amount of the promoter metal does not always yield an increased yield of any of the glycols.

The invention claimed is:

1. Process for preparing ethylene glycol from a carbohydrate source,
wherein hydrogen, the carbohydrate source, a liquid diluent and a catalyst system are introduced as reactants into a reaction zone;
wherein the catalyst system comprises a tungsten compound and ruthenium as hydrogenolysis metal and further at least one promoter metal selected from Cu, Fe, Ni, Co, Pt, Pd, Rh, and Ir;
wherein the carbohydrate source is reacted with hydrogen in the presence of the catalyst system to yield a product mixture comprising ethylene glycol and butylene glycol; and wherein butylene glycol is selectively removed from the product mixture by azeotropic distillation using an entraining agent, wherein the entraining agent is selected from the group consisting of glycerol, erythritol, sorbitol, methyl ethyl ketoxime and combinations thereof.

2. Process according to claim 1, wherein the carbohydrate source is selected from the group consisting of polysaccharides, oligosaccharides, disaccharides, and monosaccharides.

3. Process according to claim 1, wherein the catalyst system comprises a tungsten compound that has an oxidation state of at least +2.

4. Process according to claim 1, wherein the catalyst system comprises a tungsten compound selected from the group consisting of tungstic acid ($H_2WO_4$), ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxide ($WO_3$), heteropoly compounds of tungsten, and combinations thereof.

5. Process according to claim 4, wherein the catalyst system comprises tungstic acid.

6. Process according to claim 1, wherein ruthenium and the at least one promoter metal are present in the form of a catalyst supported on a carrier.

7. Process according to claim 6, wherein the carrier is selected from the group supports, consisting of activated carbon, silica, alumina, silica-alumina, zirconia, titania, niobia, iron oxide, tin oxide, zinc oxide, silica-zirconia, zeolitic aluminosilicates, titanosilicates, magnesia, silicon carbide, clays and combinations thereof.

8. Process according to claim 1, wherein the molar ratio of tungsten to ruthenium is in the range of 1 to 25.

9. Process according to claim 1, wherein the concentration of the tungsten compound is in the range of 1 to 35% by wt, calculated as tungsten and based on the weight of the carbohydrate source.

10. Process according to claim 1, wherein the amount of ruthenium as hydrogenolysis metal and the promoter metal or metals ranges from 0.2 to 1.0% by wt, calculated as the metals and based on the amount of carbohydrate source introduced into the reaction zone.

11. Process according to claim 1, wherein the carbohydrate source comprises a combination of at least one pentose-containing carbohydrate and at least one hexose-containing carbohydrate.

12. Process according to claim 1, wherein the diluent is a mixture of alkylene glycol and water, wherein the amount of alkylene glycol ranges from 2 to 25% by volume, based on the volume of water and alkylene glycol.

13. Process according to claim 12, wherein the diluent further comprises one or more compounds selected from the group consisting of sulfoxides, alcohols other than alkylene glycols, amides and mixtures thereof.

14. Process according to claim 1, wherein the temperature in the reaction zone ranges from 120 to 300° C.

15. Process according to claim 1, wherein a hydrogen partial pressure in the reaction zone is in the range of 1 to 16 MPa.

16. Process according to claim 1, wherein the average residence time of the catalyst system in the reaction zone is in the range of 5 min. to 6 hrs.

17. Process according to claim 1, wherein the amount of promoter metal or metals is at most equal to 50% by weight, based on the weight of ruthenium.

18. Process according to claim 1, wherein the weight ratio of ruthenium to promoter metal or metals is in the range of 2:1 to 100:1.

19. Process according to claim 1, wherein the catalyst system comprises a tungsten compound and ruthenium as hydrogenolysis metal and further at least one promoter metal selected from Rh, Pt, Pd, and Ir.

* * * * *